United States Patent
Scheller et al.

(10) Patent No.: US 9,645,098 B2
(45) Date of Patent: May 9, 2017

(54) DETECTION SYSTEM FOR DETECTING A SOLDERED JOINT

(71) Applicant: Robert Bosch GmbH, Stuttgart (DE)

(72) Inventors: Stefan Scheller, Schwieberdingen (DE); Torsten Hundert, Salzgitter (DE); Marco Braun, Bitzfeld (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 14/896,714

(22) PCT Filed: May 26, 2014

(86) PCT No.: PCT/EP2014/060754
§ 371 (c)(1),
(2) Date: Dec. 8, 2015

(87) PCT Pub. No.: WO2014/198520
PCT Pub. Date: Dec. 18, 2014

(65) Prior Publication Data
US 2016/0131598 A1    May 12, 2016

(30) Foreign Application Priority Data
Jun. 14, 2013   (DE) .................. 10 2013 211 090

(51) Int. Cl.
*G01N 21/952* (2006.01)
*G01N 21/956* (2006.01)
*G01N 21/64* (2006.01)
*G01N 21/88* (2006.01)

(52) U.S. Cl.
CPC ....... *G01N 21/952* (2013.01); *G01N 21/6428* (2013.01); *G01N 21/8806* (2013.01);
(Continued)

(58) Field of Classification Search
CPC ............. G01N 21/952; G01N 21/6428; G01N 21/8806; G01N 21/95684; G01N 2021/6439; G01N 2201/016
See application file for complete search history.

(56) References Cited

U.S. PATENT DOCUMENTS 4,233,620 A * 11/1980 Darrow ................ H01L 23/055
257/697
8,902,418 B2 * 12/2014 Jeong .................. G01N 21/956
356/237.5
(Continued)

FOREIGN PATENT DOCUMENTS

| EP | 2241878 | 10/2010 |
|----|---------|---------|
| EP | 2669662 | 12/2013 |
| WO | 2012101943 | 8/2012 |

OTHER PUBLICATIONS

International Search Report for Application No. PCT/EP2014/060754 dated Sep. 19, 2014 (English Translation, 3 pages).

*Primary Examiner* — Christine Sung
(74) *Attorney, Agent, or Firm* — Michael Best & Friedrich LLP

(57) ABSTRACT

The invention relates to a detection system (1) for detecting a soldered joint (16, 17) of an electronic component (10), particularly an integrated circuit. The component comprises a cuboid enclosure. The detection system comprises a detection device (2) with an emitter (5) for electromagnetic radiation and a detector (6) for the electromagnetic radiation. The detection device is designed to generate electromagnetic radiation (18, 19) with the emitter and to transmit said radiation to the component. The detector is arranged and designed to detect electromagnetic radiation (18', 19') reflected by the component and to generate an image data set representing the reflected radiation. The detection device is designed to generate from the image data set at least one (Continued)

edge data set representing one edge of the component and to determine in the region of the edge data set, particularly of an image region of the image data set representing the edge, at least one part of the image data set representing a soldered joint and to generate and output a quality signal representing a quality of the soldered joint on the basis of an intensity value, particularly a brightness or grey value of the part of the image data set.

8 Claims, 2 Drawing Sheets

(52) U.S. Cl.
CPC ............... *G01N 21/95684* (2013.01); *G01N 2021/6439* (2013.01); *G01N 2021/95646* (2013.01); *G01N 2201/061* (2013.01)

(56) References Cited

U.S. PATENT DOCUMENTS

| | | | |
|---|---|---|---|
| 9,091,668 B2* | 7/2015 | Hong | .................... G01N 21/956 |
| 2001/0012107 A1* | 8/2001 | Toh | .................. G01N 21/95684 |
| | | | 356/601 |
| 2004/0197019 A1* | 10/2004 | Van Den Broek | ... B23K 1/0016 |
| | | | 382/150 |
| 2009/0194319 A1* | 8/2009 | Itoh | .......................... G03F 7/031 |
| | | | 174/250 |
| 2013/0048357 A1* | 2/2013 | Ueta | ...................... H05K 3/287 |
| | | | 174/258 |
| 2013/0113009 A1* | 5/2013 | Kim | ........................ H01L 33/60 |
| | | | 257/98 |

* cited by examiner

DETECTION SYSTEM FOR DETECTING A SOLDERED JOINT

BACKGROUND OF THE INVENTION

The invention relates to a detection system for detecting a soldered joint of an electronic component, particularly an integrated circuit. The component comprises a cuboid enclosure. The detection system comprises a detection device with an emitter for electromagnetic radiation and a detector for the electromagnetic radiation. The detection device is designed to generate electromagnetic radiation with the emitter and to transmit said radiation to the component. The detector is arranged and designed to detect electromagnetic radiation reflected by the component and to generate an image data set representing the radiation.

In the case of detection devices for assessing the quality of electronic circuits, also referred to as AOI devices, known from the prior art, there is a problem that soldered joints of integrated circuits which have a serrated enclosure can be very difficult to detect.

SUMMARY

According to the invention, the detection device is designed to generate from the image data set at least one edge data set representing one edge of the component and to determine in the region of the edge data set, particularly of an image region of the image data set representing the edge, at least one part of the image data set representing a soldered joint and to generate and output a quality signal representing a quality of the soldered joint on the basis of an intensity value, particularly a brightness or grey value of the part of the image data set.

The detection system, particularly the detection device of the detection system of the type mentioned above, can be designed, starting from a detected edge, to locate a soldered joint with which the component is connected to the printed circuit board. A soldered joint can also be advantageously detected in this manner, in which the electrical contact of the component is located on a side facing the printed circuit board, especially on a bottom side of the component. If the soldered joint, which connects a conductor track of the printed circuit board to the contact of the component, is defective, the contact of the component is only partially or insufficiently covered with solder so that a solder ball is located beneath the component at the contact.

In the case of an intact soldered joint, the solder extends from the contact up to a conductor track and is therefore visible in a top view of the printed circuit board or can be detected by an automatic detection device. The edge of the component can, however, be advantageously detected by the detection device as a reference and starting point for locating soldered joints, whereby the detection of the soldered joints can also reliably take place when a tolerance exists in the positioning of the component on the printed circuit board.

The detection device can have a model detection unit. The model detection unit is designed to detect the edge—particularly by means of a polynomial approximation of a polynomial of the first degree. The model detection unit is preferably designed to determine the edge by means of an RLS algorithm (RLS=root least square).

In one embodiment of the invention, the detection system comprises at least one electronic component, in particular the integrated circuit comprising the cuboid, for example serrated, enclosure. The component is connected to a printed circuit board via a soldered connection. The component preferably has a coating which reflects the electromagnetic radiation starting from the edge on a side remote from the printed circuit board. As a result, the edge can be reliably detected in an advantageous manner by means of the detection device. The coating which advantageously extends to the edge can thus form a reliable detection means, in particular a contrast means for detecting the edge.

It has, in fact, been recognized that logos which are typically imprinted on the enclosure of the component cannot form a sufficiently precise determination of the position of the component on the printed circuit board and thus cannot form a sufficiently precise starting point for locating a soldered joint with which the component is connected to the printed circuit board.

In another embodiment of the invention, the coating is a color pigment, particularly a titanium dioxide. The coating can thus advantageously be easily (and without requiring a sufficient accuracy) applied to the side of the component which is remote from the printed circuit board. The edge of the component thus generates the reference line in the color image of a print job of the coating. Soldered joints can be located by the detection device starting from said reference line.

In another embodiment of the invention, the coating is fluorescently designed. In a further manner, the emitter for the electromagnetic radiation is designed to generate fluorescence generating radiation preferably independently of non-fluorescence generating radiation. In this way, the edge of the component can be advantageously detected by irradiating the printed circuit board with fluorescence generating radiation, particularly UV radiation. In order to locate the soldered joints and to further assess the quality of the soldered joint, radiation in the visible range, in particular in the wave length range between 400 and 800 nanometers, can be emitted by the detection device.

The printed circuit board, which is connected to the component, preferably has the fluorescently designed coating only in the region of the edge of the component. In an advantageous manner, the edge can thus be reliably detected by means of the unique criterion formed in this way.

The invention also relates to a method for detecting a defective soldered joint of a cuboid component which is connected to the printed circuit board by means of a soldered joint.

In the method, electromagnetic radiation is transmitted to the printed circuit board and electromagnetic radiation which is reflected at least by the component, preferably in addition by the printed circuit board, is detected. An image data set representing the reflected radiation is furthermore generated, and a part of the image data set representing an edge of the component is detected in said image data set. An edge data set corresponding to the part of the image data set can furthermore be generated. A quality of a soldered joint can be determined starting from the part representing the edge.

In another embodiment of the inventive method, the quality of the soldered joint is determined, starting from the edge, on the basis of an intensity value of a part of the image data set representing the soldered joint. In a further preferable manner, an I-O signal (I-O=in order) or a N-I-O signal (N-I-O=not in order) is generated and outputted on the basis of the quality of the soldered joint that was determined.

Starting at the edge, the component can have a coating that reflects electromagnetic radiation on a side remote from the printed circuit board.

In another embodiment, the component has, starting at the edge, a fluorescent coating on a side remote from the printed circuit board. To this end, the aforementioned reflecting coating can additionally be fluorescently designed.

Fluorescence generating radiation, particularly UV radiation, is preferably generated to detect the edge and is transmitted to the printed circuit board and the component. The edge is preferably thereupon detected on the basis of the fluorescent radiation emitted by the coating.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
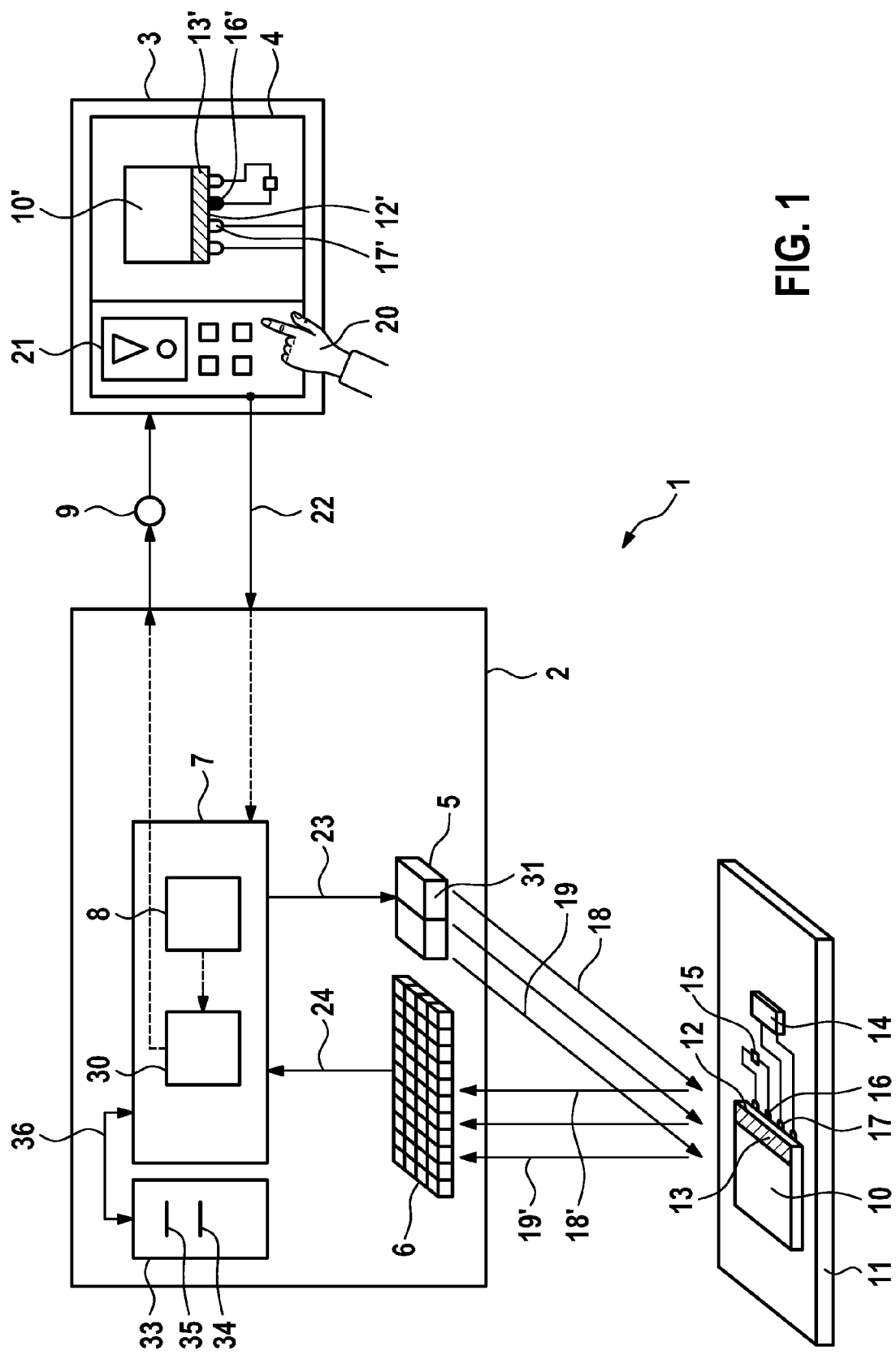
FIG. 1 shows an exemplary embodiment for a detection system, which is designed to detect an edge of the component by means of electromagnetic radiation and, starting from the edge of the component, to detect a soldered joint and to ascertain the quality of the soldered joint and to produce an output signal representing the quality of said soldered joint.

FIG. 1 shows schematically an exemplary embodiment for a detection system 1. The detection system 1 comprises a detection device 2. The detection device 2 is connected to a user interface on the output side. The user interface comprises an image reproduction unit 3, which is formed, in particular, by a TFT display (TFT=thin film transistor). The image reproduction unit 3 also comprises a touch-sensitive surface 4. On the basis of the touch-sensitive surface 4 being touched, the touch-sensitive surface 4 is designed to generate a user interaction signal representing the point of touch and to output said signal on the output side. The user-sensitive surface 4 is connected to the detection device 2 via a connection line 22. The detection device 2 comprises an emitter 5 for electromagnetic radiation 18. The emitter 5 is, for example, formed by at least one light-emitting diode, a light-emitting diode field comprising a plurality of light-emitting diodes and by a laser, for example a semiconductor laser.

The detection device 2 also comprises a detector 6 for the electromagnetic radiation 18, said detector being designed and arranged to receive reflected electromagnetic radiation 18' from a printed circuit board 11 comprising a component 10 and to generate an image data set 34 representing the reflected electromagnetic radiation 18' and output the same on the output side. The detector 6 has a multiplicity of matrix elements, each matrix element being designed to generate an output signal that represents an intensity, also referred to as radiant intensity, of the electromagnetic radiation on the basis of a received electromagnetic radiation.

The output signal is represented by the previously mentioned image data set 34 in this exemplary embodiment. The detector 6 is, for example, formed by a CCD detector (CCD=charge coupled device) and connected on the output side to a processing unit 7 via a connection line 24. The processing unit 7, which is formed, for example, by a microcontroller and a microprocessor, is designed to receive the image data set 34 via the connection line 24, which image data set represents the printed circuit board 11 comprising the component 10 and to store said image data set 34 in a storage 33 that is connected to the processing unit 7 via a connection line 36.

In addition to the component 10, the printed circuit board 11 also comprises a further electronic component 14, for example an integrated circuit, and a further component 15, for example a resistor. The component 10, which is formed, for example, by a microprocessor or an FPGA (FPGA=field programmable gate array) or an ASIC (ASIC=application specific integrated circuit, has connections on the side thereof facing the printed circuit board 11. The electrical connections are each soldered in a reflow soldering process to a corresponding solder pad, formed by a conductor track section of a conductor track of the printed circuit board 11.

In this exemplary embodiment, the component 10 is a component comprising a serrated enclosure, the enclosure having a cuboid shape. The enclosure of the component 10 has an edge 12, which forms a line, particularly a straight line, in a top view of the printed circuit board 11 and the component 10. The edge 12, which forms a straight line in a projection onto the printed circuit board 11 so that the electrical connections of the component 10 which are disposed between the component 10 and the printed circuit board 11 are shadowed by the component 10, particularly by the enclosure thereof, i.e. are hidden in a top view, can form a starting point for the detection device 2 in order to detect and further analyze soldered joints which lead to the electrical connections of the component 10.

In a top view of the printed circuit board 11, the soldered joints lead away from the edge 12. A soldered joint 17 is depicted to which solder has been applied and which represents in the image data set generated by the detector 6 at the location corresponding to the soldered joint 17 an intensity value of the reflected electromagnetic radiation 18 which corresponds to the soldered joint 17. A defective soldered joint 16 is also depicted, to which solder has not been applied and which generates an intensity value by means of the reflected electromagnetic radiation which value corresponds to the defective soldered joint 16.

The detection device 2, in particular the processing unit 7, has a model detection unit 8 in this exemplary embodiment. The model detection unit is designed to detect the edge 12 in the image data set 34 generated by the detector 6 and to generate an edge data set that represents the edge and to store said edge data set in the storage 33. To this end, the model detection unit 8 can, for example, be designed to ascertain the edge by means of a polynomial approximation of a polynomial of the first degree.

The component 10 has a coating 13 in the region of the edge 12 on a side remote from the printed circuit board 11. In this exemplary embodiment, the coating 13 has pigments, for example titanium dioxide. In this way, the edge 12 can be detected by the detection unit 2 in a simple manner by means of the boundary formation criterion of the boundary delimiting the coating 13 that is generated by the edge 12 itself. The model detection unit 8 can thus detect the edge 12 in a simple manner by means of the image contrast generated by means of the coating 13. Starting from the edge 12, the model detection unit 8 can detect the soldered joints, such as the soldered joints 16 and 17, which, in a top view of the printed circuit board, extend outwardly away from the edge 12 in this exemplary embodiment.

The detection device 2 is designed in this exemplary embodiment to transmit on the output side the image data set detected by the detector 6 to the image reproduction unit 3 via an output 9. The image reproduction unit 3 shows the component 10', visible to the human eye, the coating 13' which is depicted by the image reproduction unit 3 and extends up to the edge 12', the defective soldered joint 16' and the intact soldered joint 17'. In this exemplary embodiment, the processing unit 7 has detected the defective soldered joint 16 and generated an error signal on the basis of the defective detection result and transmitted the error signal via the output 9 to the image reproduction unit 3. The image reproduction unit 3 displays a warning symbol 21 which indicates that the detection device 2 has detected a defective soldered joint.

The detection device 2 can, for example, detect the printed circuit board 11 by means of a user interaction signal, generated by the touch-sensitive surface 4 for example generated by a user's hand and in addition actuate the emitter 5 by means of the processing unit 7 via a connection line 23 to generate and transmit the electromagnetic radiation 18.

The emitter 5 comprises, in this exemplary embodiment, two mutually different radiation sources, namely a radiation source 31, which, for example, is formed by at least one or a plurality of light-emitting diodes and which is designed to generate and transmit electromagnetic radiation, such as the electromagnetic radiation 18, that can, for example, be perceived as white by the human eye. In this exemplary embodiment, the emitter 5 also has a radiation source which is designed to generate ultraviolet electromagnetic radiation 19. The ultraviolet electromagnetic radiation 19 has, for example, a wave length of less than 400 nanometers. The radiation source is, for example, formed by a mercury vapor lamp or a lightemitting diode, for example an aluminum nitride light-emitting diode or an aluminum-galliumnitride light-emitting diode, which is designed to generate and transmit electromagnetic radiation with a wave length between 250 and 365 nanometers. The ultraviolet electromagnetic radiation 19, which, for example, cannot be detected by the human eye and cannot be detected by the detector 6 in this exemplary embodiment, strikes the coating 13 of the component 10.

The coating 13 also has, in this exemplary embodiment, a fluorescently designed color pigment. Fluorescent radiation in a wave length range that can be detected by the detector 6, for example between 400 and 800 nanometers, can thus be generated and transmitted from the coating 13. The fluorescent radiation beam 19' which strikes the detector 6 is depicted.

The processing unit 7 is, for example, designed to actuate the emitter 5 via the connection line 23 in order to generate the ultraviolet electromagnetic radiation 19. The radiation source 26 of the emitter 5 can then generate the ultraviolet electromagnetic radiation 19 and transmit said radiation to the printed circuit board 11. By means of the image of the printed circuit board 11 which was thus generated by means of fluorescence, a reflection radiation 19' alone can be detected by the detector 6 in a simple manner, whereby the edge 12 can be simply detected in the image. In a subsequent step, the processing unit 7 can activate the emitter 5 via the connection line 23 to generate, for example, white or red electromagnetic radiation 18. By means of the electromagnetic radiation 18 generated in this manner, an image data set can then be generated by means of the detector 6, said image data set representing a detailed image and thus intensity values for each object location on the printed circuit board 11. With the aid of said image data set, it is possible to differentiate between an intact soldered joint 17 and a defective soldered joint 16.

Figure 2:
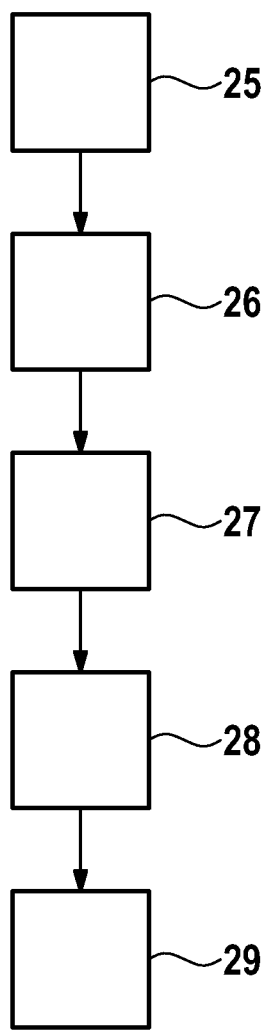
FIG. 2 shows an example for a method for detecting a defective soldered joint.

FIG. 2 shows a method for detecting a soldered joint which connects a connection of a cuboid component, such as the component 10 depicted in FIG. 1, to a printed circuit board 11.

To this end, electromagnetic radiation is generated in a first step 25 by means of an emitter for electromagnetic radiation and transmitted to the printed circuit board and the component. In a further step 26, reflected electromagnetic radiation is detected by the printed circuit board and an image data set is generated, which represents the printed circuit board in particular by means of mutually different intensity values.

In a further step 27, an edge of the component is determined in particular by means of a model detection unit.

Starting from the edge previously determined in step 27, a soldered joint is detected in a further step 28. In a further step 29, the quality of the soldered joint is determined, in particular to determine whether the soldered joint is an intact soldered joint or a defective, in particular cold, soldered joint.

To this end, the processing unit 7 depicted in FIG. 1 can have a soldered joint discriminator 30 which is designed to distinguish between an intact and defective soldered joint on the basis of an intensity value represented by a part of the image data set and to generate a I-O signal or a N-I-O signal and emit the same on the output side as a function of a result of the decision.

The detection device 2, in particular processing device 7, depicted in FIG. 1 can additionally comprise the aforementioned soldered joint discriminator 30. The output signal generated by the soldered joint discriminator 30 can be transmitted from the detection device 2 on the output side via the output 9 to the image reproduction unit 3 and there be reproduced, for example, by means of a warning symbol 21 in the event of the N-I-O signal.

The invention claimed is:

1. A detection system for detecting a soldered joint of an electronic component having a cuboid enclosure, the detection system comprising:
   at least one electronic component, wherein the at least one electronic component is connected to a printed circuit board by the soldered joint and the at least one electronic component has a coating, wherein the coating reflects electromagnetic radiation and starts at an edge of the electronic component, on a side facing away from the printed circuit board;
   a detection device with an emitter configured to generate and transmit said electromagnetic radiation to the at least one electronic component; and
   a detector configured to
      detect reflected electromagnetic radiation that is reflected by the at least one electronic component, and
      generate an image data set representing the reflected electromagnetic radiation,
   wherein the detection device is further configured to
      generate, from the image data set, at least one edge data set representing one edge of the at least one electronic component,
      determine, in a region of the at least one edge data set, at least one part of the image data set representing the soldered joint, and generate and output a quality signal representing a quality of the soldered joint on a basis of an intensity value of the at least one part of the image data set.

2. The detection system according to claim 1, wherein the detection device further comprises a model detection unit designed to determine the edge of the at least one electronic component by a polynomial approximation of a polynomial of the first degree.

3. The detection system according to claim 1, wherein the coating has a color pigment.

4. The detection system according to claim 1, wherein the coating is fluorescently designed.

5. The detection system according to claim 4, wherein the emitter is designed to generate the electromagnetic radiation that generates fluorescence independently of the electromagnetic radiation that does not generate fluorescence.

6. A method for detecting a defective soldered joint of a cuboid component which is connected to a printed circuit board by a soldered joint, the method comprising:
   transmitting electromagnetic radiation to the printed circuit board and the cuboid component;
   detecting the electromagnetic radiation that is reflected by the cuboid component;
   generating an image data set representing reflected electromagnetic radiation;
   detecting a part of the image data set representing an edge of the cuboid component; and
   determining a quality of the soldered joint starting from the part of the image data set representing the edge,
   wherein the cuboid component, starting from the edge, has a coating which reflects the electromagnetic radiation on a side remote from the printed circuit board.

7. The method according to claim 6, wherein, starting from the edge, the quality of the soldered joint is determined on a basis of an intensity value of the part of the image data set representing the soldered joint and an I-O signal or a N-I-O signal is generated and outputted on a basis of the quality of the soldered joint that is determined.

8. The method according to claim 6, wherein the coating is an electromagnetic radiation generating fluorescent coating, wherein fluorescent radiation from the electromagnetic radiation generating fluorescent coating is generated from the electromagnetic radiation that is transmitted to the printed circuit board and the cuboid component, and wherein the edge is detected on a basis of the fluorescent radiation that is reflected.

* * * * *